US008568482B2

(12) United States Patent
Kraus et al.

(10) Patent No.: US 8,568,482 B2
(45) Date of Patent: Oct. 29, 2013

(54) HEIGHT-ADJUSTABLE IMPLANT TO BE INSERTED BETWEEN VERTEBRAL BODIES AND CORRESPONDING HANDLING TOOL

(76) Inventors: Kilian Kraus, Werneck (DE); Norbert Saal, Thundorf (DE)

( * ) Notice: Subject to any disclaimer, the term of this patent is extended or adjusted under 35 U.S.C. 154(b) by 773 days.

(21) Appl. No.: 10/556,200

(22) PCT Filed: May 11, 2004

(86) PCT No.: PCT/EP2004/005046
§ 371 (c)(1),
(2), (4) Date: Aug. 16, 2006

(87) PCT Pub. No.: WO2004/100837
PCT Pub. Date: Nov. 25, 2004

(65) Prior Publication Data
US 2007/0028710 A1    Feb. 8, 2007

(30) Foreign Application Priority Data

May 14, 2003    (DE) .................................. 103 21 534

(51) Int. Cl.
*A61F 2/44* (2006.01)
*A61F 2/46* (2006.01)
*A61B 17/88* (2006.01)

(52) U.S. Cl.
USPC ........ 623/17.16; 606/99; 606/914; 623/17.15

(58) Field of Classification Search
USPC .............. 623/17.11–17.16; 403/109.1, 109.4; 254/103, 236
See application file for complete search history.

(56) References Cited

U.S. PATENT DOCUMENTS

| 1,238,863 | A | * | 9/1917 | Willour ........................ 254/103 |
| 1,486,723 | A |   | 7/1921 | Bernson |
| 1,645,570 | A |   | 6/1924 | Anderson |
| 1,896,715 | A | * | 2/1933 | Martinetti ........................ 254/1 |
| 2,702,453 | A |   | 2/1955 | Mercier |
| 3,987,499 | A |   | 10/1976 | Scharbach et al. |
| 4,657,550 | A |   | 4/1987 | Daher |
| 4,932,975 | A |   | 6/1990 | Main et al. |
| 4,961,740 | A |   | 10/1990 | Ray et al. |
| 5,026,373 | A |   | 6/1991 | Ray et al. |
| 5,055,104 | A |   | 10/1991 | Ray |
| 5,236,460 | A |   | 8/1993 | Barber |
| 5,246,458 | A |   | 9/1993 | Graham |
| 5,571,192 | A |   | 11/1996 | Schonhoffer |
| 5,575,790 | A |   | 11/1996 | Chen et al. |
| 5,665,122 | A |   | 9/1997 | Kambin |
| 5,702,449 | A |   | 12/1997 | McKay |

(Continued)

FOREIGN PATENT DOCUMENTS

DE    3023942    5/1985
DE    3729600    3/1989

(Continued)

*Primary Examiner* — Michael T Schaper
(74) *Attorney, Agent, or Firm* — Workman Nydegger

(57) ABSTRACT

A height-adjustable implant is designed to be inserted between vertebral bodies and includes a first and a second sleeve part. The second sleeve part carries an external thread and is inserted with a longitudinal section thereof in the first sleeve part in a rotationally fixed and axially movable manner. On its longitudinal section projecting from the first sleeve part, the second sleeve part is encompassed by a nut that engages with the external thread. The nut carries a toothed ring. The invention also relates to a tool for handling the implant.

24 Claims, 6 Drawing Sheets

(56) References Cited

U.S. PATENT DOCUMENTS

| | | |
|---|---|---|
| 5,702,453 A | 12/1997 | Rabbe et al. |
| 5,702,455 A | 12/1997 | Saggar |
| 5,723,013 A | 3/1998 | Jeanson et al. |
| 5,772,661 A | 6/1998 | Michelson |
| 5,776,197 A | 7/1998 | Rabbe et al. |
| 5,776,198 A | 7/1998 | Rabbe et al. |
| 5,782,919 A | 7/1998 | Zdeblick et al. |
| 5,885,299 A | 3/1999 | Winslow et al. |
| 5,888,228 A | 3/1999 | Knothe et al. |
| 5,904,719 A | 5/1999 | Errico et al. |
| 5,916,267 A | 6/1999 | Tienboon |
| 5,951,553 A | 9/1999 | Betz et al. |
| 5,980,522 A | 11/1999 | Koros et al. |
| 5,989,290 A | 11/1999 | Biedermann et al. |
| 6,004,326 A | 12/1999 | Castro et al. |
| 6,015,436 A | 1/2000 | Schonhoffer |
| 6,042,582 A | 3/2000 | Ray |
| 6,077,267 A | 6/2000 | Huene |
| 6,086,595 A | 7/2000 | Yonemura et al. |
| 6,086,613 A | 7/2000 | Camino et al. |
| 6,113,638 A | 9/2000 | Williams et al. |
| 6,120,503 A | 9/2000 | Michelson |
| 6,129,763 A | 10/2000 | Chauvin et al. |
| 6,156,040 A | 12/2000 | Yonemura et al. |
| 6,176,881 B1 | 1/2001 | Schar et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,200,348 B1 * | 3/2001 | Biedermann et al. ...... 623/17.11 |
| 6,214,050 B1 | 4/2001 | Huene |
| 6,267,763 B1 | 7/2001 | Castro |
| 6,287,308 B1 | 9/2001 | Betz et al. |
| 6,296,665 B1 | 10/2001 | Strnad et al. |
| 6,299,644 B1 | 10/2001 | Vanderschot |
| D450,122 S | 11/2001 | Michelson |
| 6,315,795 B1 | 11/2001 | Scarborough et al. |
| 6,315,975 B1 | 11/2001 | Lindblad |
| 6,344,057 B1 | 2/2002 | Rabbe et al. |
| 6,375,683 B1 | 4/2002 | Crozet et al. |
| 6,395,034 B1 | 5/2002 | Suddaby |
| 6,419,706 B1 | 7/2002 | Graf |
| 6,428,575 B2 | 8/2002 | Koo et al. |
| 6,436,142 B1 | 8/2002 | Paes et al. |
| 6,443,989 B1 | 9/2002 | Jackson |
| 6,443,990 B1 | 9/2002 | Aebi et al. |
| 6,451,057 B1 | 9/2002 | Chen et al. |
| 6,454,806 B1 | 9/2002 | Cohen et al. |
| 6,454,807 B1 | 9/2002 | Jackson |
| 6,471,724 B2 | 10/2002 | Zdeblick et al. |
| 6,478,795 B1 | 11/2002 | Gournay et al. |
| 6,511,484 B2 | 1/2003 | Torode et al. |
| 6,520,991 B2 | 2/2003 | Heune |
| 6,524,341 B2 | 2/2003 | Lang et al. |
| 6,527,805 B2 | 3/2003 | Studer et al. |
| 6,544,265 B2 | 4/2003 | Lieberman |
| 6,551,319 B2 | 4/2003 | Lieberman |
| 6,554,265 B2 | 4/2003 | Andronica |
| 6,562,041 B1 | 5/2003 | Yonemura et al. |
| 6,562,074 B2 | 5/2003 | Gerbec et al. |
| 6,576,016 B1 | 6/2003 | Hochshuler et al. |
| 6,579,290 B1 | 6/2003 | Hardcastle et al. |
| 6,582,432 B1 | 6/2003 | Michelson |
| 6,582,468 B1 | 6/2003 | Gauchet |
| 6,616,695 B1 | 9/2003 | Crozet et al. |
| 6,641,614 B1 | 11/2003 | Wagner et al. |
| 6,660,038 B2 | 12/2003 | Boyer et al. |
| 6,695,760 B1 | 2/2004 | Winkler et al. |
| 6,706,070 B1 | 3/2004 | Wagner et al. |
| 6,719,796 B2 | 4/2004 | Cohen et al. |
| 6,730,088 B2 | 5/2004 | Yeh |
| 6,749,613 B1 | 6/2004 | Conchy et al. |
| 6,752,832 B2 | 6/2004 | Neumann |
| 6,758,862 B2 | 7/2004 | Berry et al. |
| 6,758,863 B2 | 7/2004 | Estes et al. |
| 6,766,798 B2 | 7/2004 | Herres et al. |
| 6,776,798 B2 | 8/2004 | Camino et al. |
| 6,779,353 B2 | 8/2004 | Hu et al. |
| 6,783,526 B1 | 8/2004 | Lin et al. |
| 6,783,528 B2 | 8/2004 | Vincent-Prestigiacomo |
| 6,783,547 B2 | 8/2004 | Castro |
| 6,796,984 B2 | 9/2004 | Soubeiran |
| 6,805,714 B2 | 10/2004 | Sutcliffe |
| 6,808,537 B2 | 10/2004 | Michelson |
| 6,814,756 B1 | 11/2004 | Michelson |
| 6,830,589 B2 | 12/2004 | Erickson |
| 6,835,206 B2 | 12/2004 | Jackson |
| 6,852,129 B2 | 2/2005 | Gerbec et al. |
| 6,855,168 B2 | 2/2005 | Crozet |
| 6,863,673 B2 | 3/2005 | Gerbec et al. |
| 6,866,664 B2 | 3/2005 | Schar et al. |
| 6,866,682 B1 | 3/2005 | An et al. |
| 6,896,512 B2 | 5/2005 | Rattner et al. |
| 6,899,734 B2 | 5/2005 | Castro et al. |
| 6,905,512 B2 | 6/2005 | Paes et al. |
| 6,908,485 B2 | 6/2005 | Crozet et al. |
| 6,921,403 B2 | 7/2005 | Cragg et al. |
| 6,923,810 B1 | 8/2005 | Michelson |
| 6,923,830 B2 | 8/2005 | Michelson |
| 6,960,232 B2 | 11/2005 | Lyons et al. |
| 6,976,949 B2 | 12/2005 | Winkler et al. |
| 6,979,353 B2 | 12/2005 | Bresina |
| 6,991,653 B2 | 1/2006 | White et al. |
| 6,991,654 B2 | 1/2006 | Foley |
| 7,008,453 B1 | 3/2006 | Michelson |
| 7,018,412 B2 | 3/2006 | Ferreira et al. |
| 7,018,415 B1 | 3/2006 | McKay |
| 7,022,138 B2 | 4/2006 | Mashburn |
| 7,025,787 B2 | 4/2006 | Bryan et al. |
| 7,029,498 B2 | 4/2006 | Boehm et al. |
| 7,033,392 B2 | 4/2006 | Schmiel et al. |
| 7,056,343 B2 | 6/2006 | Schafer et al. |
| 7,094,257 B2 | 8/2006 | Mujwid et al. |
| 7,097,648 B1 | 8/2006 | Globerman et al. |
| 7,118,590 B1 | 10/2006 | Cronin |
| 7,118,598 B2 | 10/2006 | Michelson |
| 7,147,665 B1 | 12/2006 | Bryan et al. |
| 7,156,874 B2 | 1/2007 | Paponneau et al. |
| 7,166,130 B2 | 1/2007 | Ferree |
| 7,166,131 B2 | 1/2007 | Studer et al. |
| 7,182,781 B1 | 2/2007 | Bianchi et al. |
| 7,192,446 B2 | 3/2007 | Shapiro et al. |
| 7,192,496 B2 | 3/2007 | Wojcik |
| 7,217,291 B2 | 5/2007 | Zucherman et al. |
| 7,235,105 B2 | 6/2007 | Jackson |
| 7,255,714 B2 | 8/2007 | Malek |
| 7,273,498 B2 | 9/2007 | Bianchi et al. |
| 7,282,063 B2 | 10/2007 | Cohen et al. |
| 7,285,134 B2 | 10/2007 | Berry et al. |
| 7,285,135 B2 | 10/2007 | McKay et al. |
| 7,303,583 B1 | 12/2007 | Schar et al. |
| 7,303,584 B2 | 12/2007 | Castro et al. |
| 7,309,358 B2 | 12/2007 | Berry et al. |
| 7,311,733 B2 | 12/2007 | Metz-Stavenhagen |
| 7,316,686 B2 | 1/2008 | Dorchak et al. |
| 7,320,708 B1 | 1/2008 | Bernstein |
| 7,322,982 B2 | 1/2008 | Vincent-Prestigiacomo |
| 7,329,283 B2 | 2/2008 | Estes et al. |
| 7,331,994 B2 | 2/2008 | Gordon et al. |
| 7,335,200 B2 | 2/2008 | Carli |
| 7,364,589 B2 | 4/2008 | Eisermann |
| 7,381,178 B2 | 6/2008 | Winkler et al. |
| 7,384,431 B2 | 6/2008 | Berry |
| 7,407,513 B2 | 8/2008 | Alleyne et al. |
| 7,410,501 B2 | 8/2008 | Michelson |
| 2001/0012966 A1 | 8/2001 | Studer et al. |
| 2001/0031965 A1 | 10/2001 | Zucherman et al. |
| 2001/0056302 A1 | 12/2001 | Boyer et al. |
| 2002/0010511 A1 | 1/2002 | Michelson |
| 2002/0068976 A1 | 6/2002 | Jackson |
| 2002/0068977 A1 | 6/2002 | Jackson |
| 2002/0068978 A1 | 6/2002 | Camino et al. |
| 2002/0082695 A1 | 6/2002 | Neumann |
| 2002/0138142 A1 * | 9/2002 | Castro et al. ............... 623/17.11 |

(56) References Cited

U.S. PATENT DOCUMENTS

| | | |
|---|---|---|
| 2003/0045877 A1 | 3/2003 | Yeh |
| 2003/0108272 A1 | 6/2003 | Sherrer et al. |
| 2003/0130739 A1 | 7/2003 | Gerbec et al. |
| 2003/0176925 A1 | 9/2003 | Paponneau |
| 2003/0181980 A1 | 9/2003 | Berry et al. |
| 2003/0191531 A1 | 10/2003 | Berry et al. |
| 2003/0191535 A1 | 10/2003 | Castro |
| 2003/0191555 A1 | 10/2003 | Tekehara et al. |
| 2003/0208272 A1 | 11/2003 | Crozet et al. |
| 2004/0044411 A1 | 3/2004 | Suddaby |
| 2004/0054412 A1 | 3/2004 | Gerbec et al. |
| 2004/0073314 A1 | 4/2004 | White et al. |
| 2004/0153156 A1 | 8/2004 | Cohen et al. |
| 2004/0153160 A1 | 8/2004 | Carrasco |
| 2004/0167626 A1 | 8/2004 | Geremakis et al. |
| 2004/0172129 A1 | 9/2004 | Schafer et al. |
| 2004/0225366 A1 | 11/2004 | Eisermann et al. |
| 2004/0249466 A1 | 12/2004 | Liu et al. |
| 2004/0267364 A1 | 12/2004 | Carli et al. |
| 2005/0004572 A1 | 1/2005 | Biedermann et al. |
| 2005/0027359 A1 | 2/2005 | Mashburn |
| 2005/0033437 A1 | 2/2005 | Bao et al. |
| 2005/0060036 A1 | 3/2005 | Schultz et al. |
| 2005/0060037 A1 | 3/2005 | Michelson |
| 2005/0143820 A1 | 6/2005 | Zucherman et al. |
| 2005/0143821 A1 | 6/2005 | Zdeblick et al. |
| 2005/0143825 A1 | 6/2005 | Enayati |
| 2005/0209697 A1 | 9/2005 | Paponneau et al. |
| 2005/0228500 A1 | 10/2005 | Kim et al. |
| 2006/0058877 A1 | 3/2006 | Gutlin et al. |
| 2006/0058879 A1 | 3/2006 | Metz-Stavenhagen |
| 2006/0069442 A1 | 3/2006 | Michelson |
| 2006/0100710 A1* | 5/2006 | Gutlin et al. ............... 623/17.15 |
| 2006/0116770 A1 | 6/2006 | White et al. |
| 2006/0129241 A1 | 6/2006 | Boyer et al. |
| 2006/0149385 A1 | 7/2006 | McKay |
| 2006/0200244 A1 | 9/2006 | Assaker |
| 2006/0241770 A1* | 10/2006 | Rhoda et al. ............... 623/17.15 |
| 2007/0028710 A1 | 2/2007 | Kraus et al. |
| 2007/0106385 A1 | 5/2007 | Zucherman et al. |
| 2007/0168036 A1 | 7/2007 | Ainsworth et al. |
| 2007/0191951 A1 | 8/2007 | Branch |
| 2007/0191954 A1* | 8/2007 | Hansell et al. ............. 623/17.15 |
| 2008/0015698 A1 | 1/2008 | Marino et al. |
| 2008/0015700 A1 | 1/2008 | Zucherman et al. |
| 2008/0021560 A1 | 1/2008 | Zucherman et al. |
| 2008/0021561 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0046088 A1 | 2/2008 | Zucherman et al. |
| 2008/0046089 A1 | 2/2008 | Zucherman et al. |
| 2008/0051904 A1 | 2/2008 | Zucherman et al. |
| 2008/0051905 A1 | 2/2008 | Zucherman et al. |
| 2008/0054904 A1 | 3/2008 | Neufeld et al. |
| 2008/0058941 A1 | 3/2008 | Zucherman et al. |
| 2008/0065086 A1 | 3/2008 | Zucherman et al. |
| 2008/0071378 A1 | 3/2008 | Zucherman et al. |
| 2008/0103602 A1 | 5/2008 | Berry et al. |
| 2008/0172057 A1 | 7/2008 | Zucherman et al. |
| 2008/0183210 A1 | 7/2008 | Zucherman et al. |

FOREIGN PATENT DOCUMENTS

| | | |
|---|---|---|
| DE | 4423257 | 1/1996 |
| DE | 19509317 | 9/1996 |
| DE | 19519101 | 11/1996 |
| DE | 196 22 827 A | 12/1997 |
| DE | 69317654 | 10/1998 |
| DE | 19816782 | 10/1999 |
| DE | 19841252 | 3/2000 |
| DE | 100 65 232 A1 | 7/2002 |
| DE | 101 27 924 C | 12/2002 |
| DE | 10210214 | 9/2003 |
| EP | 0144667 | 6/1985 |
| EP | 01219266 | 11/2001 |
| EP | 0716840 | 5/2002 |
| EP | 1501453 | 2/2005 |
| FR | 2666221 | 3/1992 |
| JP | 2261446 | 10/1990 |
| JP | 02261446 | 10/1990 |
| WO | 9857601 | 12/1998 |
| WO | 0023013 | 4/2000 |
| WO | 0024327 | 5/2000 |
| WO | WO 01/72246 A | 10/2001 |

* cited by examiner

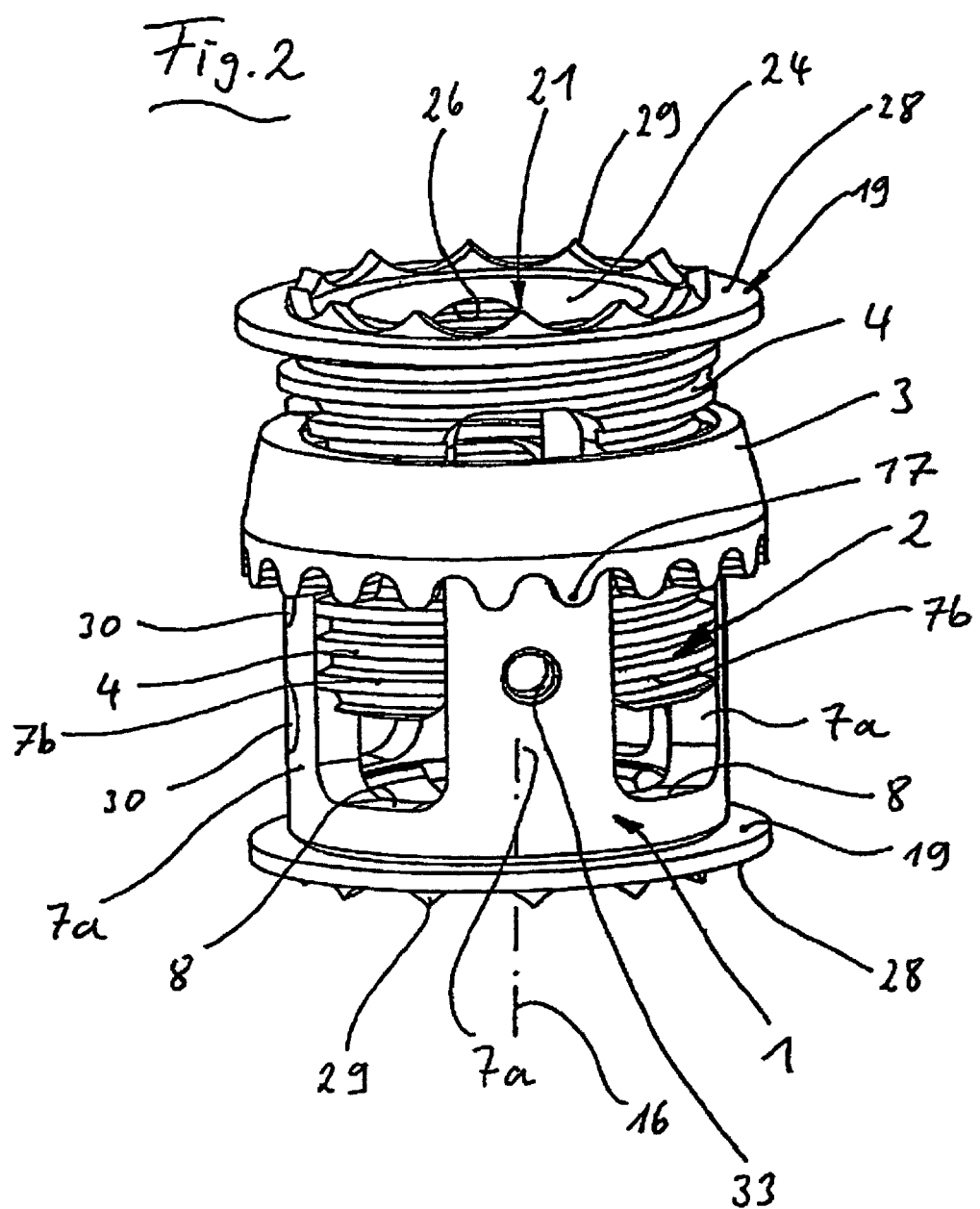

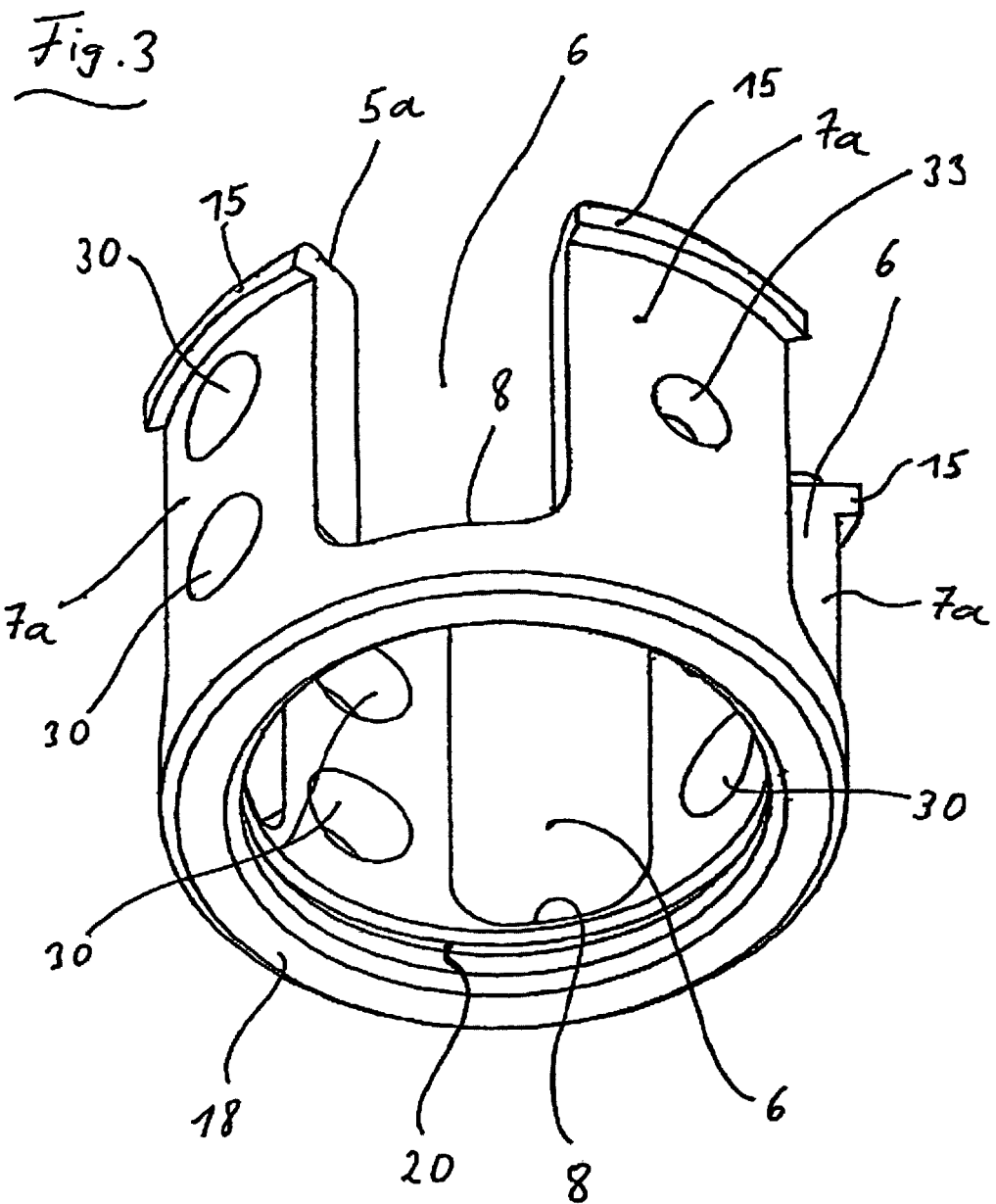

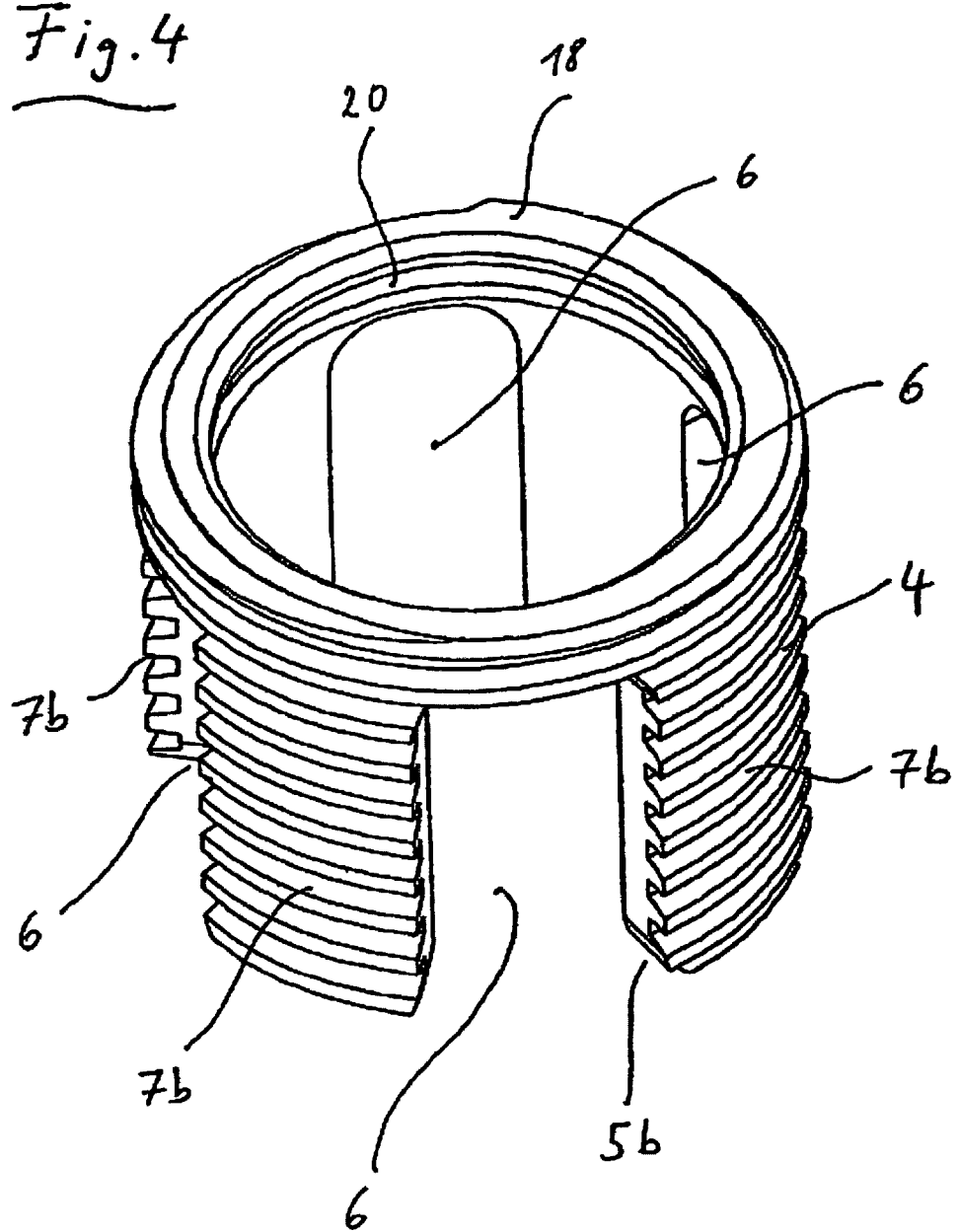

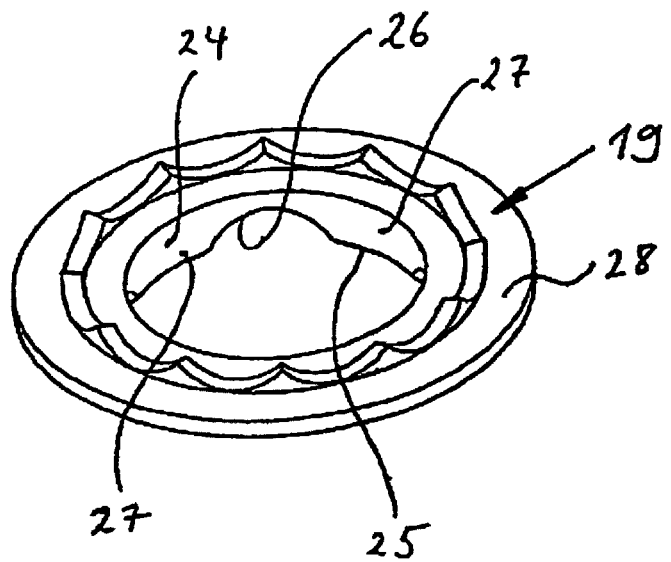
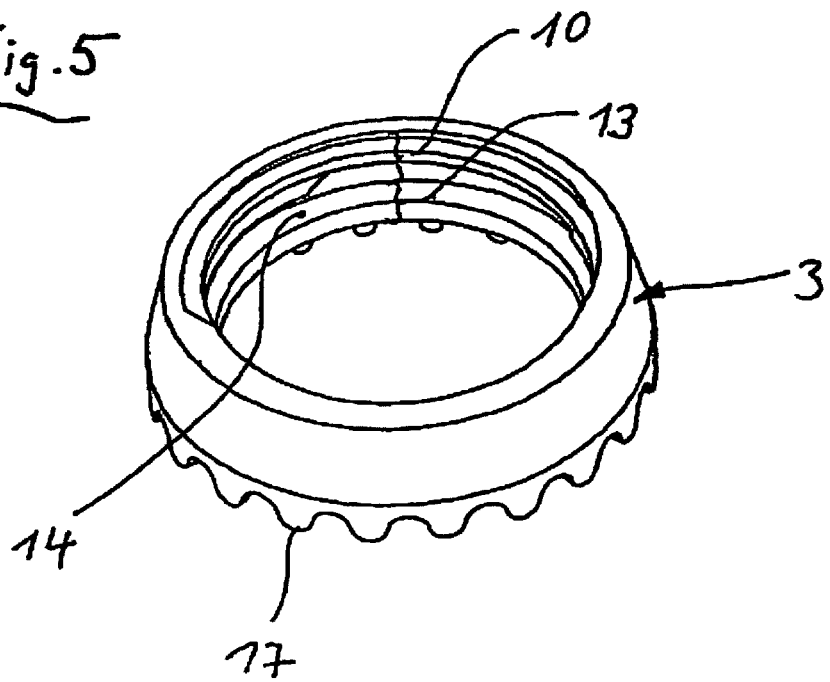

HEIGHT-ADJUSTABLE IMPLANT TO BE INSERTED BETWEEN VERTEBRAL BODIES AND CORRESPONDING HANDLING TOOL

BACKGROUND OF THE INVENTION

1. Field of the Invention

The invention relates to a height-adjustable implant for insertion between vertebral bodies and a tool suitable for the manipulation thereof.

2. Present State of the Art

An implant known from patent specification DE 196 22 827 A1, for example, has a first and a second sleeve part, which second sleeve part has an external thread which is placed in the first sleeve part by means of a longitudinal portion so as to be prevented from rotating and axially displaceable whilst its longitudinal portion projecting out from the first sleeve part is enclosed by a nut engaging in the external thread. When the nut is rotated, the second sleeve part is moved out of the first sleeve part. In order to operate the nut, a rod-shaped manipulating tool is inserted by its free end in a recess on the external circumference of the nut. By pivoting the tool in a plane extending transversely to the longitudinal axis of the implant, the nut is turned by a further distance corresponding to the pivot angle of the tool. The tool is then extracted from the nut and the process described above is repeated until the implant is at the requisite height. During the operation of turning the nut, the first sleeve part must not turn as well and as a rule, it therefore has to be held still by means of another tool. The height adjustment of the known implant therefore requires extra time and technical equipment. Furthermore, a relatively large orifice is needed for the operation in order to perform the described manipulations unobstructed.

SUMMARY OF THE INVENTION

Against the background of the above, the objective of the invention is to propose an implant and a manipulating tool which facilitates insertion in the vertebral column.

The nut of the implant bears a toothed ring and is therefore designed as a gear. The height of the implant can be adjusted with the aid of a tool incorporating an appropriate complementary element, for example a driving gear, in which case there is no need to perform any pivoting movements with the manipulating tool. Furthermore, the tool does not have to be repositioned several times. Instead, it can be held in one and the same position during the entire process of making the height adjustment, which significantly simplifies the operation and reduces the time needed for the operation.

In order to guarantee that the first sleeve part is secured to prevent it from rotation, it is provided with a threaded bore, where the manipulating tool driving the nut can be secured. Unlike conventional implants, therefore, only a single tool is needed both to drive the nut and to immobilise the first sleeve part.

In the case of the implant known from patent specification DE 196 22 827 A1, the nut is supported on the end face of the first sleeve part directed towards it as the second sleeve part is moved out. However, the nut is not otherwise secured on the first sleeve part. Consequently, the height of the known implant can only be increased but not reduced, i.e. the second sleeve part can not be moved into the first sleeve part. In the case of the implant proposed by the invention, on the other hand, the nut is secured on the first sleeve part by means of an axially acting positive connection, in other words in both axial directions, as a result of which it is possible both to increase and reduce the implant height. The latter may be necessary if too big a height adjustment was made after inserting the implant, for example.

In a particularly preferred example of an embodiment of the invention, the two sleeve parts have axially extending windows opening in their mutually facing ends, in which case the peripheral portions disposed between two adjacent windows lie so as to be axially displaceable in the windows of the other respective sleeve part. The advantage of this compared with an arrangement in which the two sleeve parts engage concentrically one inside the other is that less material is necessary and the implant is therefore more lightweight overall. Furthermore, a significantly larger interior is available, which can be filled with bone material or similar. Due to the fact that the two sleeve parts mesh with one another like a comb, they are ultimately guaranteed to be fixedly secured, preventing mutual rotation.

A radially widened end plate is provided as a means of supporting the implant on a vertebral body. In a preferred embodiment, this is a separate, releasably fixed part. The appropriate end plate, for example one with a flat plane extending at an angle to the mid-longitudinal axis of the implant, may be used in each individual case. If the end plate is secured on the sleeve part by means of a snap-fit connection, a secure mount on the sleeve part can be guaranteed on the one hand, whilst making replacement easy on the other hand. In one embodiment which is simple from the point of view of production and assembly, an annular groove is provided in the internal wall of the sleeve part close to the end face, in which catch lugs integrally moulded on the underside of the end plate locate.

A manipulating tool for the implant described above has a gear co-operating with the nut. A retaining mechanism is preferably provided on the manipulating tool as a means of holding the implant immobile. The gear is disposed so that its axis extends transversely to the axis of the toothed ring of the nut during the driving operation. As mentioned above, a deflection of the rotating movement of the drive axis is not necessary. In one arrangement that is particularly compact and easy to operate, the toothed ring is disposed on the end face of a tubular portion and the tubular portion has a rod extending through it, the free end of which projects out from the tubular portion and can be screwed into the threaded bore of the first sleeve part. The coaxial disposition of the tubular portion and the rod results in a compact manipulating tool that is easy to operate.

BRIEF DESCRIPTION OF THE DRAWINGS

The invention will now be described in more detail with reference to the appended drawings. Of these:

FIG. 2 shows the implant illustrated in FIG. 1 with the second sleeve part partially extracted, FIG. 3 is a perspective view of the first sleeve part, FIG. 4 is a perspective view of the extractable second sleeve part, FIG. 5 shows a nut used to drive the first sleeve part, FIG. 6 shows an end plate which can be fixed on a sleeve part.

DETAILED DESCRIPTION OF THE PREFERRED EMBODIMENTS

Figure 1:
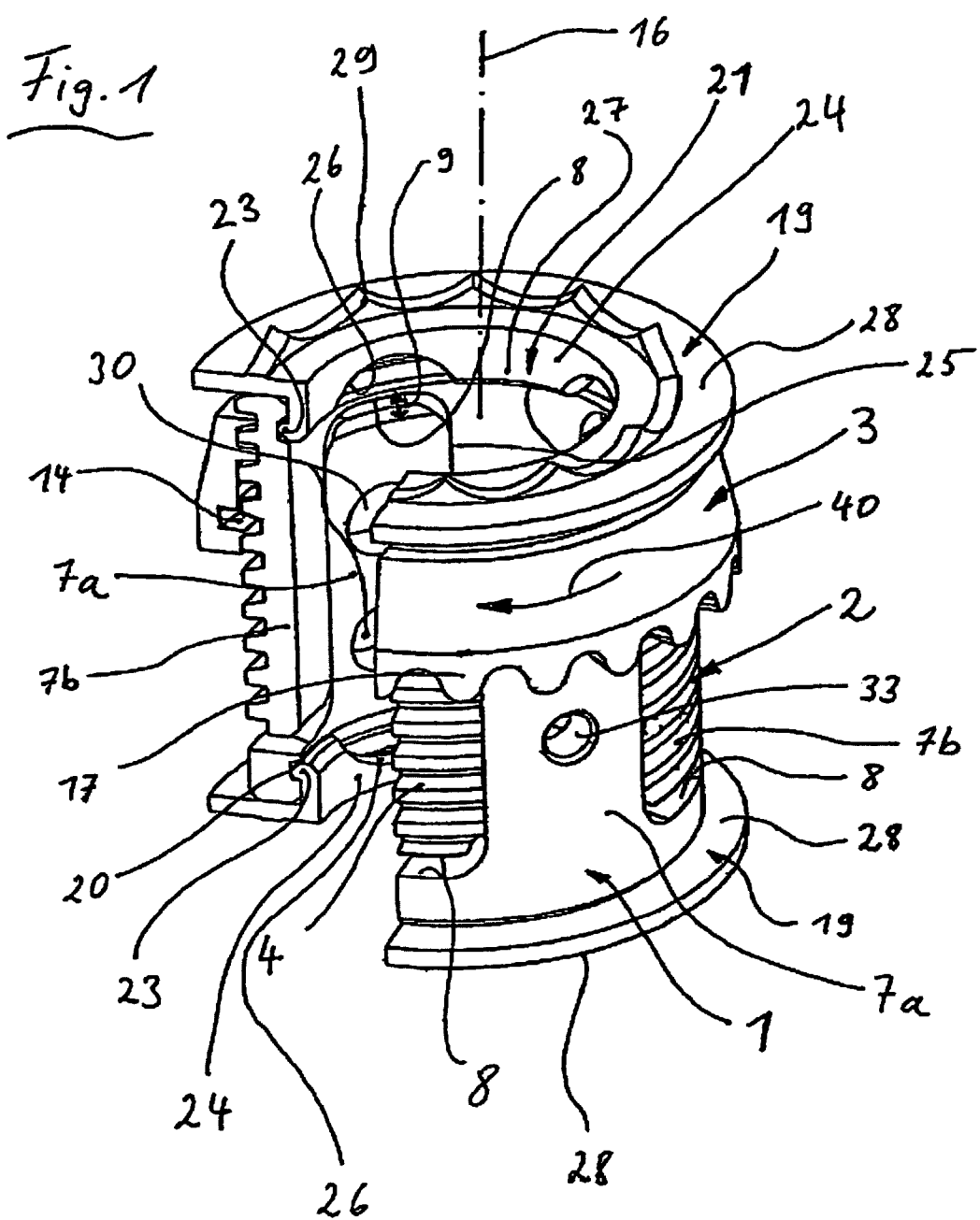
FIG. 1 is a perspective view with a partially cut-away section of an implant comprising a first sleeve part and a second sleeve part lying inside it and axially displaceable therein, the second sleeve part being shown in its inserted position.

The implant illustrated in the drawings comprises a first sleeve part 1, a second sleeve part 2 and a nut 3 as its main components. The sleeve part 2 is provided with an external thread 4 extending essentially across its entire length. Both sleeve parts 1, 2 have axially extending windows 6 which open into their mutually facing end face 5a, b in the assembled state. The peripheral portions 7a, b left between two adjacent windows lie so as to be axially displaceable in the windows 6 of the other respective sleeve part 1, 2. This being the case, the clearance between the peripheral portions 7a, b is dimensioned so as to guarantee that the two sleeve parts will sit without wobbling but easily slide one inside the other. The sleeve parts 1, 2 have a more or less identical wall thickness and the same internal diameter, i.e. the peripheral portions 7b of the second sleeve part 2 do not project beyond the external circumference or beyond the internal circumference of the sleeve part 1. The axial length of the windows 6 and peripheral portions 7a, b is dimensioned so that there is an axial distance 9 between the end face 5a, b of a peripheral portion 7a, b and the base 8 of a sleeve part 1, 2 when the sleeve part 2 is inserted to its maximum.

The nut 3, which encloses both sleeve parts 1, 2, is used to adjust the height and move the sleeve part 2 in and out. The nut 3 is connected to the first sleeve part 1 so as to be axially immobile and rotatable. The internal face of the nut 3 enclosing the two sleeve parts 1, 2 has an upper longitudinal portion provided with an internal thread 10 and a longitudinal portion 13 with no thread adjoining it. Incorporated in the longitudinal portion 13 is an annular groove 14. The nut 3 is positioned on the sleeve part 1 so that only the thread-free longitudinal portion 13 is disposed enclosing the peripheral portions 7a of the sleeve part 1 and the internal thread 10 engages with the external thread 4 of the sleeve part 2. Close to the end face 5a of the peripheral portion 7a of the sleeve part 1 is an integrally formed segment-shaped projection 15 extending across the entire width of the peripheral portion 7a, which locates in the annular groove 14 of the nut. Consequently, although the nut 3 is able to rotate on the sleeve part 1, it is immobilised on it in both axial directions. The side of the nut 3 facing the free ends of the peripheral portions 7b of the sleeve part 2 bears a toothed ring 17 extending coaxially with the mid-longitudinal axis 16 of the implant. The toothed ring 17 is integral with the nut 3, formed by milling for example. Its purpose is to displace the nut 3 in rotation with the aid of a tool, which will be described in more detail below, and thus move the sleeve part 2 out of the sleeve part 1 or into it, in other words, to adjust the height of the implant.

The end faces 18 remote from the free ends of the peripheral portions 7a, b bear an end plate 19 standing radially out beyond the periphery of the sleeve parts 1, 2. The end plates 19 can be releasably secured on the sleeve parts 1, 2 with the aid of a snap-fit connection. To this end, an annular groove 20 is provided on the internal face of the sleeve parts 1, 2, close to their end faces 18, in which catch projections 23 provided on the side of the end plate facing the end faces 18a, b locate. The catch projections 23 are integrally formed on an apron 24 bounding a central orifice 21 in the end plate 19. Provided in the edge 25 of the apron 24 are several recesses 26 distributed uniformly in the circumferential direction. The circumferential portions 27 disposed between the recesses 26 support the catch projections 23. The circumferential portions 27 can be elastically deflected radially, slightly towards the interior, thereby facilitating the fitting or removal of the end plate 19. Projecting out from the external faces 28 of the end plates 19 in the direction of the longitudinal axis 16 is a toothed ring 29. It is used to anchor the implant on a vertebral body.

Disposed in the peripheral portions 7a are two orifices 30. The orifices 30 and the central orifice 21 in the end plates 19 are used for filling with bone material, bone cement or similar. A radially oriented threaded bore 33 is provided in one of the peripheral portions 7a, close to the nut 3. It is used as a means of securing the manipulating tool described below.

Figure 7:
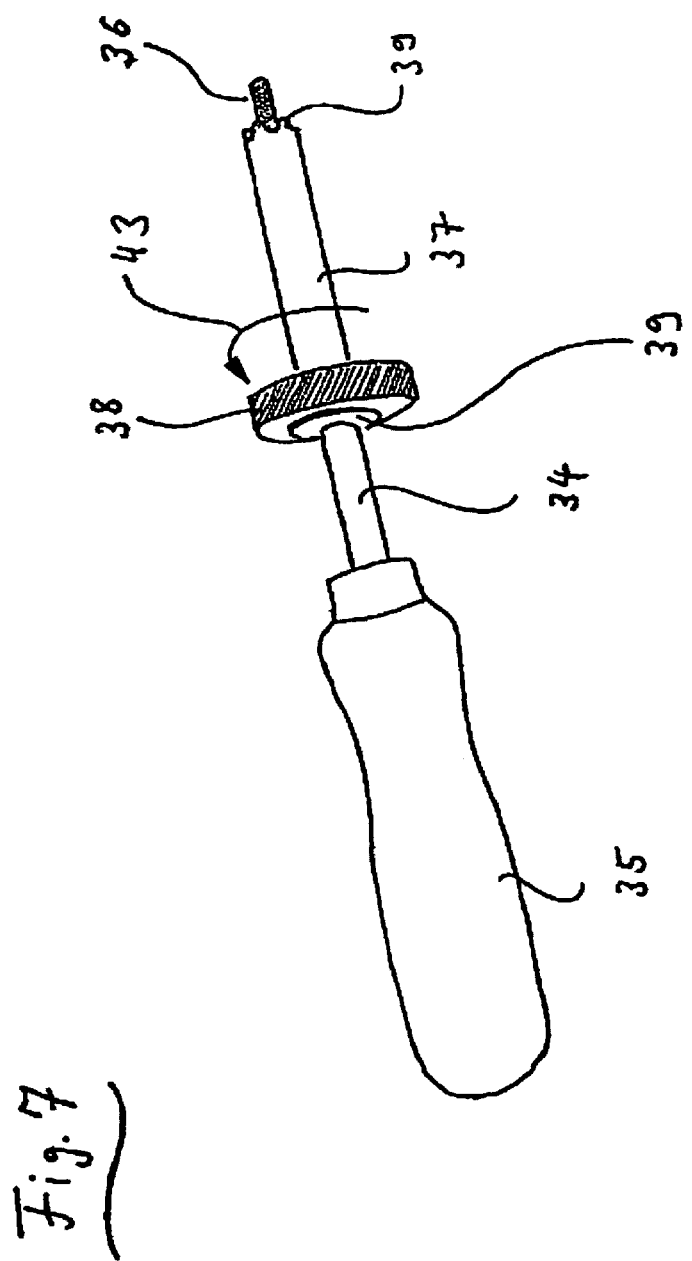
FIG. 7 shows a tool for manipulating the implant.

As may be seen from FIG. 7 the manipulating tool essentially consists of a rod 34, one end of which bears a handle 35 and the other end of which bears a threaded portion 36. The region of the rod 34 extending away from the threaded portion 36 is coaxially enclosed by a rotating sleeve 37. The end of the rotating sleeve 37 facing the handle 35 bears a knurled wheel 38 and the oppositely lying end a toothed ring 39. The toothed ring 39 is produced, like the nut 3, by milling the sleeve end face. An axial displacement of the sleeve 37 in the direction towards the handle 35 is restricted by means of a stop flange 39.

In order to adjust the height of the implant, for example starting from the situation illustrated in FIG. 1, the manipulating tool is turned in the threaded bore 33 by means of its threaded portion 36. As this takes place, the toothed ring 39 engages with the toothed ring 17 in the manner of a crown gear, i.e. the axis of the toothed ring 39 extends essentially perpendicular to the axis of the toothed ring 17. This being the case, the knurled wheel 38 lies in abutment with the stop flange 29.

Once the implant has been inserted through an operation orifice in the vertebral column with the aid of the manipulating tool, the rotating sleeve 37 is displaced by rotating the knurled wheel 38 in order to set the implant at a bigger height. If the external thread 4 of the sleeve part 2 and the internal thread 10 of the nut 3 are right-hand threads, the nut 3 must be turned in the direction of arrow 40 and the knurled wheel turned in the direction of arrow 43. In order to release the manipulating tool from the implant, its threaded portion 36 is removed from the threaded bore 33 by turning the handle 35. Since the sleeve 37 is able to rotate about the rod 34, there is no need to hold the rotating sleeve immobile during turning for removal from the threaded portion 36. Once the two sleeve parts 1, 2 have been positioned relative to one another, the position can be fixed in various ways. One simple option is to screw a screw (not illustrated) into the threaded bore 33 more or less by a tip.

LIST OF REFERENCE NUMBERS

1 First sleeve part
2 Second sleeve part
3 Nut
4 External thread
5a,b End face
6 Window
7a,b Peripheral portion
  (a=first sleeve part;
  b=second sleeve part)
8 Base
9 Axial distance
10 Internal thread
13 Longitudinal portion
14 Annular groove
15 Projection
16 Mid-longitudinal axis
17 Toothed ring
18 End face
19 End plate 20 Annular groove
21 Orifice
23 Catch projection
24 Apron
25 Edge
26 Recess
27 Circumferential portion
28 External face
29 Toothed ring
30 Orifice
33 Threaded bore
34 Rod
35 Handle
36 Threaded portion
37 Rotating sleeve
38 Knurled wheel
39 Stop flange
40 Arrow
43 Arrow

The invention claimed is:

1. An implant kit, comprising:
a height-adjustable implant for insertion between vertebral bodies, comprising:
   a first sleeve part having an outwardly facing surface with a bore formed thereon, the first sleeve part extending longitudinally from a proximal end to a distal end;
   a second sleeve part having a longitudinal portion with an external thread, the longitudinal portion at least partially lying in the first sleeve part so that the second sleeve part is prevented from rotating relative to the first sleeve part but is axially displaceable relative to the first sleeve part, the longitudinal portion of the second sleeve part having an inside surface bounding an internal cavity;
   a nut having a first toothed ring and an internal thread, the internal thread of the nut engaging with the external thread of the second sleeve part distal of the distal end of the first sleeve part;
   an end plate releasably fixed to an end face of the first sleeve part or the second sleeve part intended to be placed against a vertebral body, the end plate being secured to the end face; and
a manipulating tool comprising:
   a rod extending into the bore on the outwardly facing surface of the first sleeve part and being removably fixed to the first sleeve part without passing through the internal cavity of the second sleeve part; and
   a second toothed ring rotatably encircling the rod and releasably engaging the first toothed ring so that rotation of the second toothed ring while the rod is fixed to the first sleeve part facilitates rotation of the nut.

2. The implant kit as claimed in claim 1, wherein the first toothed ring is disposed on a side of the nut which faces the first sleeve part.

3. The implant kit as claimed in claim 1, wherein the nut is secured on the first sleeve part by an axially acting positive connection.

4. The implant kit as claimed in claim 1, wherein the first sleeve part and the second sleeve part have mutually facing ends and a plurality of peripheral portions defining axially extending windows opening at the mutually facing ends, each peripheral portion of one of the first sleeve part and the second sleeve part lying in a separate window of the other one of the first sleeve part and the second sleeve part so as to be axially displaceable.

5. The implant kit as claimed in claim 1, wherein an annular groove is formed near the end face in an internal wall of the first sleeve part or the second sleeve part and catch lugs are integrally formed on the end plate.

6. The implant kit as claimed in claim 1, wherein the second toothed ring of the manipulating tool is disposed so that when a height of the implant is adjusted, the axis of the second toothed ring of the manipulating tool extends transversely to the axis of the first toothed ring of the nut.

7. The implant kit as claimed in claim 1, wherein the second toothed ring of the manipulating tool is disposed on an end face of a rotating sleeve, and wherein the rod extends through the rotating sleeve, the rod having an end face which projects out from the end face of the rotating sleeve, and wherein the rod includes a threaded portion screwed into the bore of the first sleeve part of the implant to removably fix the rod to the first sleeve part.

8. The implant kit as claimed in claim 1, wherein the rod has a threaded end that is threaded into the bore on the outwardly facing surface of the first sleeve part without passing through the internal cavity to removably fix the rod to the first sleeve part.

9. The implant kit as claimed in claim 1, wherein the first toothed ring of the nut encircles the outwardly facing surface of the first sleeve part.

10. The implant kit as claimed in claim 1, wherein the nut has a rotational axis about which the nut rotates, and the rod does not intersect the rotational axis when the rod is secured within the bore.

11. The implant kit as claimed in claim 1, wherein the first toothed ring of the nut has an inner diameter that is larger than the diameter of the outwardly facing surface of the first sleeve part, such that the first toothed ring completely encircles the outwardly facing surface of the first sleeve part.

12. The implant kit according to claim 1, further comprising projections outwardly extending from arms of the first sleeve part, the projections being received within an annular groove formed on an internal surface of the nut.

13. The implant kit as claimed in claim 1, wherein the first sleeve part and the second sleeve part have approximately the same wall thickness and the same internal diameter.

14. The implant kit as claimed in claim 1, wherein the end plate is secured to the end face by a snap-fit connection.

15. An intervertebral implant kit comprising:
an intervertebral implant comprising:
   a first sleeve part comprising a circular first base and a plurality of first arms projecting axially from the first base, each pair of adjacent first arms at least partially bounding a first window therebetween, a projection radially outwardly extending from each first arm, the projection having a first side and a second side axially opposed to the first side, a bore being formed on an exterior surface of at least one of the first arms;
   a second sleeve part comprising a circular second base and a plurality of second arms projecting from the second base, the plurality of second arms having an exterior surface with an external thread formed thereon and an opposing interior surface, each pair of adjacent second arms at least partially bounding a second window therebetween, the first arms of the first sleeve part being received within the second windows of the second sleeve part and the second arms of the second sleeve part being received within the first windows of the first sleeve part so that the first sleeve part is prevented from rotating relative to the second sleeve part, the interior surface of the second sleeve part bounding an internal cavity; and a nut having an internal surface extending between a first end face and a second end face, an internal thread and an annular groove being formed on the internal surface, the projections of the first arms being received within the annular groove such that the first and second sides of the projections are positioned within the annular groove, the first end face having a plurality of teeth formed thereon, the nut encircling the second sleeve part so that the internal thread of the nut threadedly engages the external thread of the second sleeve part; and a manipulating tool for axially displacing the implant, the manipulating tool comprising:

a tubular rotatable sleeve longitudinally extending between a proximal end and an opposing distal end, the rotatable sleeve having a plurality of teeth formed on the distal end thereof; and a rod longitudinally extending through the rotatable sleeve, the rotatable sleeve being rotatable about the rod, the rod having a distal end that is configured to be selectively received into the bore of the first sleeve part, and to be removably fixable to the first sleeve part without the rod passing through the internal cavity, wherein when the rod is received within the bore, the plurality of teeth formed on the rotatable sleeve engage the plurality of teeth formed on the first end face of the nut such that rotation of the rotatable sleeve while the rod is fixed to the first sleeve part causes rotation of the nut.

16. The intervertebral implant kit according to claim 15, further comprising an end plate releasably fixed to the first sleeve part or the second sleeve part.

17. The kit according to claim 15, wherein a rotational axis of the rotatable sleeve is substantially perpendicular to the rotational axis of the nut.

18. The intervertebral implant kit according to claim 15, wherein the nut encircles the first sleeve part and the second sleeve part.

19. The intervertebral implant kit according to claim 15, wherein the plurality of first arms of the first sleeve part have an exterior surface, and wherein the nut is rotatable about a rotational axis, the first end face of the nut extending radially further than the exterior surface of the first sleeve part so that the plurality of teeth are radially disposed further away from the rotational axis than the exterior surface of the plurality of first arms.

20. The intervertebral implant kit as claimed in claim 15, further comprising an end plate releasably fixed to an end face of the first sleeve part or the second sleeve part intended to be placed against a vertebral body, the end plate being secured to the end face by a snap-fit connection.

21. The intervertebral implant kit as claimed in claim 15, wherein the first sleeve part and the second sleeve part have approximately the same wall thickness and the same internal diameter.

22. An intervertebral implant kit comprising:
an intervertebral implant comprising:
a first sleeve part comprising a circular first base and a plurality of first arms projecting axially from the first base, each pair of adjacent first arms at least partially bounding a first window therebetween, a projection radially outwardly extending from each first arm, the projection having a first side and a second side axially opposed to the first side, a bore being formed on an exterior surface of at least one of the first arms;
a second sleeve part comprising a circular second base and a plurality of second arms projecting from the second base, the plurality of second arms having an exterior surface with an external thread formed thereon and an opposing interior surface, each pair of adjacent second arms at least partially bounding a second window therebetween, the first arms of the first sleeve part being received within the second windows of the second sleeve part and the second arms of the second sleeve part being received within the first windows of the first sleeve part so that the first sleeve part is prevented from rotating relative to the second sleeve part, the interior surface of the second sleeve part bounding an internal cavity; and a nut having an internal surface extending between a first end face and a second end face, an internal thread and an annular groove being formed on the internal surface, the projections of the first arms being received within the annular groove such that the first and second sides of the projections are positioned within the annular groove, the first end face having a plurality of teeth formed thereon, the nut encircling the second sleeve part so that the internal thread of the nut threadedly engages the external thread of the second sleeve part; and a manipulating tool comprising:
a rod configured to extend into the bore on the exterior surface of at least one of the first arms of the first sleeve part and to be removably fixable to the first sleeve part without passing through the internal cavity; and a toothed ring rotatably encircling the rod and being configured to releasably engage the plurality of teeth formed on the nut so that rotation of the toothed ring while the rod is fixed to the first sleeve part facilitates rotation of the nut.

23. The intervertebral implant kit according to claim 22, wherein the rod has a threaded end that is configured to be threaded into the bore without passing through the internal cavity to removably fix the rod to the first sleeve part.

24. An intervertebral implant kit comprising:
an intervertebral implant comprising:
a first sleeve part comprising a circular first base and a plurality of first arms projecting distally from the first base to a distal end, each pair of adjacent first arms at least partially bounding a first window therebetween;

a second sleeve part comprising a circular second base and a plurality of second arms projecting proximally from the second base to a proximal end, the plurality of second arms having an exterior surface with an external thread formed thereon and an opposing interior surface, each pair of adjacent second arms at least partially bounding a second window therebetween, the first arms of the first sleeve part being received within the second windows of the second sleeve part and the second arms of the second sleeve part being received within the first windows of the first sleeve part so that the first sleeve part is prevented from rotating relative to the second sleeve part, the interior surface of the second sleeve part bounding an internal cavity; and a nut having an internal surface extending between a proximal end and a distal end, a proximal end face and a distal end face being positioned respectively at the proximal and distal ends of the nut, an internal thread being formed on the internal surface, the proximal end face having a plurality of teeth formed thereon, the nut encircling the second sleeve part so that the internal thread of the nut threadedly engages the external thread of the second sleeve part distal of the distal end of the first sleeve part; and a manipulating tool comprising:
- a rod configured to be removably fixable to the first sleeve part without passing through the internal cavity; and
- a toothed ring rotatable encircling the rod and being configured to releasable engage the plurality of teeth formed on the nut so that rotation of the toothed ring while the rod is fixed to the first sleeve part facilitates rotation of the nut.

* * * * *

UNITED STATES PATENT AND TRADEMARK OFFICE
CERTIFICATE OF CORRECTION

PATENT NO.       : 8,568,482 B2                                       Page 1 of 1
APPLICATION NO.  : 10/556200
DATED            : October 29, 2013
INVENTOR(S)      : Kraus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 972 days.

Signed and Sealed this
Fifteenth Day of September, 2015

Michelle K. Lee
*Director of the United States Patent and Trademark Office*